US006480734B1

United States Patent
Zhang et al.

(10) Patent No.: US 6,480,734 B1
(45) Date of Patent: Nov. 12, 2002

(54) CARDIAC ARRHYTHMIA DETECTOR USING ECG WAVEFORM-FACTOR AND ITS IRREGULARITY

(75) Inventors: Xu-Sheng Zhang, Santa Ana Heights, CA (US); Dongping Lin, Irvine, CA (US)

(73) Assignee: Cardiac Science Inc., Irvine, CA (US)

( * ) Notice: Subject to any disclaimer, the term of this patent is extended or adjusted under 35 U.S.C. 154(b) by 13 days.

(21) Appl. No.: 09/609,558

(22) Filed: Jun. 30, 2000

(51) Int. Cl.[7] .............................................. A61B 5/04
(52) U.S. Cl. ...................................................... 600/518
(58) Field of Search ................................ 600/516, 517, 600/518; 607/4, 5, 14, 25, 9

(56) References Cited

U.S. PATENT DOCUMENTS 5,086,772 A * 2/1992 Larnard et al. ............. 128/419
5,447,519 A    9/1995 Peterson .................... 607/5

* cited by examiner

Primary Examiner—George R. Evanisko
Assistant Examiner—Frances P. Oropeza
(74) Attorney, Agent, or Firm—Gottlieb, Rackman & Reisman, P.C.

(57) ABSTRACT

A cardiac monitor is provided that monitors the condition of the heart of a cardiac patient and generates signals indicating one of several conditions, such as supraventricular tachycardia, ventricular tachycardia and ventricular fibrillation. In order to generate these signals, the ECG from the patient is analyzed to determine a cardiac interval and heart rate, as well as a waveform factor and a waveform factor irregularity. The waveform factor is derived from the average of the ECG amplitudes during a cardiac interval and the peak value of the ECG during the same interval. Preferably, a running average is calculated over several intervals. This waveform factor is then used to detect shockable ventricular arrhythmia. The waveform factor irregularity is indicative of the variability of the waveform factor and is used to differentiate between ventricular tachycardia and ventricular defibrillation.

20 Claims, 7 Drawing Sheets

CARDIAC ARRHYTHMIA DETECTOR USING ECG WAVEFORM-FACTOR AND ITS IRREGULARITY

BACKGROUND OF THE INVENTION

A. Field of Invention

The present invention relates generally to a cardiac arrhythmia detector in a prosthesis such as an internal or external cardiac defibrillator and pacemaker. More specifically, such a detector comprises a microprocessor used to perform an arrhythmia detection algorithm that detects and analyzes an ECG waveform factor and its irregularity for promptly and accurately discriminating among various types of cardiac arrhythmias, including ventricular fibrillation (VF), ventricular tachycardia (VT), supraventricular tachycardia (SVT), or other arrhythmias.

B. Description of the Prior Art

Sudden cardiac arrest (SCA) accounts for about 76% of sudden non-traumatic deaths in adults and about 50% of all cardiac deaths. Approximately 350,000 Americans experience SCA each year with only about 5% national survival rate. Even in hospital, the percentage of patients who survive SCA is not encouraging. This percentage has remained stable at approximately 15%, and has not improved in the last 30 years. Thus SCA still represents a major and unresolved public health problem.

Ventricular tachyarrhythmia (which includes ventricular fibrillation (VF) and ventricular tachycardia (VT)) is the most common initial incidence of SCA. Unlike other life-threatening conditions such as cancer or AIDS, there is an effective, inexpensive and standard therapy for SCA: timely cardioversion/defibrillation applied by a cardiac stimulator device. Early timely cardioversion/defibrillation (i.e., immediately after onset) is the key to survival, since the chances of success are reduced by 10 percent for every minute of delay of the treatment. Death usually follows unless a normal heart rhythm is restored within 5–7 minutes. Therefore, it is the lack of warning, i.e. detection, and the delay for intervention, not a lack of effective treatment, that accounts for the high death rate following SCA.

The most effective means of saving SCA victims outside a hospital consists of widespread deployment of public access defibrillators as suggested by American Heat Association, and wearable automatic external defibrillators. For diagnosed SCA high-risk patients or SCA survivals, implantable cardioverter defibrillator (ICD) is also an effective treatment. For in-hospital SCA, self-monitoring, self-evaluating, and self-defibrillating monitors, such as fully automatic external defibrillator/monitor Powerheart® (Cardiac Science, Inc., Irvine, Calif.), and automatic defibrillator module plugged into the existing modular monitoring systems, are the expected effective tools. For both implantable and external automatic defibrillators, the tachyarrhythmia detection algorithm plays the key role for the device's safety, reliability, effectiveness, ease of use, extent of automatic operations, and widespread acceptance. Prompt and accurate detection of VT and VF is still a major challenge in the defibrillation art. Different tachycardias require different electrical therapies: no electrical therapy needed for the conditions like sinus rhythm, sinus tachycardia (ST), and supraventricular tachycardia (SVT); a comparatively low-energy cardioversion for VT; and a high-energy defibrillation shock for VF. Therefore, the challenge for an effective and successful arrhythmia detector is to discriminate these three types of arrhythmias reliably and accurately. A cardiac device can then treat the appropriate condition on an "as-needed" basis. In this way, the false shocks caused by SVT and ST can be avoided, since it causes unnecessary patient distress, and may initiate VT or VF when none previously existed. Moreover, unnecessary treatment applied by an ICD also wastes power.

Differentiating VT from VF makes it allow the treatment of tachyarrhythmia with the lowest energy levels, least painful electrical stimulation pulses, and potentially the most effective therapies. For implantable devices where power source energy and patient tolerance to repeated cardioversion/defibrillation shocks are both limited, therefore, discrimination among these three types of arrhythmias is necessary and important.

Among the methods most widely used for detection of VT & VF in antitachycardia devices is heart rate (HR), and the rate of change of rate or suddenness of onset of tachycardias. Rate stability and sustained high rate also are suggested as additional criteria. Rate and rate-related measures are not a reliable criterion because of difficulty in separating SVT, VT, and VF, due to the overlap of the heart rate for these arrhythmias and the likelihood of missing an R-wave trigger (i.e., ECG dropout) during VF with rapidly changing peak amplitudes.

Another known criterion, the probability density function which was used as the original ICD detection scheme to measure of time the signal is away from the isoelectric baseline, is being gradually abandoned due to its lack of specificity for tachyarrhythmia discrimination.

Along with rate, shape differentiation between ventricular electrograms during sinus rhythm (SR) and VT and VF is another known criteria that can be expected to provide an accurate discrimination using a morphology-based algorithm with correlation analysis and template matching. However, its shortcoming is the necessity of waveform alignment, which is critical to a proper point-by-point comparison. If the test and template signals are not aligned correctly, the result of the waveform comparison can be erroneous. Moreover, aligning the test and template signals and the calculation programs can be a burdensome and time-consuming problem, especially for implantable cardioverter/defibrillator. Furthermore, more memory is required for storing the test and template signals. Therefore, there is still some difficulties for real-time implementation in defibrillators, especially for ICD.

A method of discriminating among cardiac rhythms of supraventricular and ventricular origin by exploiting the differences in their underlying nonlinear dynamics reflected in the morphology of the waveform is disclosed in U.S. Pat. No. 5,645,070, issued to Turcott. A two-channel scatter diagram analysis algorithm for distinguishing VT from VF is disclosed in U.S. Pat. No. 5,404,880, issued to Throne. The shortcoming for these methods is still the computationally complex and more memory requirement. Other algorithms for tachyarrhythmia discrimination utilizing statistical methods were also proposed (Thakor et al., Ventricular Tachycardia And Fibrillation Detection By A Sequential Hypothesis Testing Algorithm, IEEE Trans. Biomed. Eng., 1990, 37:837–843 and Turner et al., Statistical Discriminant Analysis of Arrhythmias Using Intracardiac Electrograms, IEEE Trans. Biomed. Eng., 1993, 40:985–989). However, their effectiveness and practical feasibility still need further investigation.

Modulation domain function (MDF) is effective in discriminating SVT from ventricular tachyarrhythmias (Mattioni et al., Initial Clinical Experience With A Fully Automatic In-hospital External Cardioverter Defibrillator, PACE 1999, 22:1648–1655). However, SVT with an underlying chronic bundle branch block or with aberrant conduction can result in high MDF values, this method may fail for this kind of rhythm. Moreover, MDF cannot differentiate VT from VF.

Currently, AED's in use are 90% sensitive for ventricular tachyarrhythmia and 90–95% specificity for other heart rhythms. For ICD the percentage of patients who are paced or shocked unnecessarily still exceeds 40% of those receiving ICD therapies. Moreover, discrimination of VT from VF is also a difficulty objective to achieve using existing algorithms. A need still exists for discovering additional information from ECG waveform to develop computationally simple method of discriminating SVT, VT, and VF.

In atrial and ventricular tachyarrhythmias, the shapes of the P-waves and QRS-waves are distorted from the normal sinus rate shapes. Nonshockable arrhythmias have different morphology with shockable arrhythmias (VT and VF). In fact, while physicians classify a cardiac rhythm, they examine the morphology of the ECG in addition to the heart rate. The morphological differences of the cardiac waveform are indicative of cardiac condition changes. One simple and quantitative measurement for the morphological difference is the waveform-factor (WF) disclosed in this invention. Based on WF and waveform-factor irregularity (WFI), one novel cardiac arrhythmia detector is proposed for simultaneously discriminating SVT, VT, and VF.

The new algorithm of present invention as disclosed herein is simple, computationally efficient, effective, and well suited for real-time implementation. Therefore, it offers all the desirable features for the practical application to AED and ICD.

OBJECTIVES AND SUMMARY OF THE INVENTION

The present invention relates to a cardiac device with a detector that applies waveform factor analysis to physiological signals. An example of the application is to respond to the needs of AED and ICD by providing a cardiac arrhythmia detector, which provides a clearer and more reliable indication of the onset of VT and VF than has been available in the prior art.

It is accordingly an objective of the present invention to provide a cardiac device which can distinguish reliably among VT, VF, and a set of conditions comprising normal sinus rhythm (NSR), sinus tachycardia (ST), and other supraventricular tachycardias (SVT).

A further objective of the present invention is to provide such a detector which is capable of correctly and accurately distinguishing in real time among these three kinds of cardiac episodes using an easy-to-implement algorithm with a minimum amount of computation complexity.

An additional object of the present invention is to provide such a detector which quantifies the nature of VT and VF (higher waveform-factor, WF, compared to SVT) and the nature of VF (higher waveform-factor irregularity, WFI, compared to VT) in order to achieve a diagnosis.

It is still another further object of the present invention to provide such a detector, which discriminates VT from VF and thereby allowing consideration of lower energy therapies for VT to provide significant energy savings for the battery powered device and improved patient comfort, such as an implantable cardioverter/defibrillator, and at the same time avoiding unnecessary shock to SVT.

These and other objects of the invention are realized by providing a novel cardiac device with an arrhythmia detector, which is capable of reliably and efficiently differentiating VT, VF, and nonshockable SVT and atrial fibrillation (AF). Specifically, the detector of the present invention uses ECG waveform-factor and its irregularity for VT, VF, and SVT separation. According to the present invention, ECG under different cardiac rhythms demonstrates different morphology and different comparative change in waveform, which can be characterized by waveform-factor (WF) and waveform-factor irregularity (WFI). For nonshockable tachyarrhythmias (such as SVT and atrial fibrillation), their ECG WF is lower than that of VT and VF. For VT, its WFI is lower than that of VF, since the waveform of VT is more stable and the QRS complexes of VT basically look more similar than that of VF. The detector of the present invention is able to address the limitation of existing algorithms and provide accurate separation among VT, VF, and SVT.

This invention offers a considerable improvement over current methods of analysis by employing a new criterion for reliable separation among VT, VF, and SVT. Particularly, the disclosed WF and WFI measurements quantify the ECG waveform morphology and its change, where lower WF indicates nonshockable SVT and AF, and for shockable tachyarrythmias lower WFI indicates VT, higher WFI indicating VF. In this way, the method determines the precise arrhythmia allowing exact therapeutic selection. Specifically, with proper distinction of SVT, VT, and VF could benefit patients by avoidance of false shock and consideration of lower energy therapies, thereby providing patient comfort and significant energy savings (for ICD). In comparison with known methods of identifying arrhythmias, for the first time the present invention proposes the concepts of ECG WF and WFI and their estimation methods, and for the first time realizes them in a novel arrhythmia detection algorithm.

In one aspect, the present invention provides a cardiac monitor for determining the cardiac condition of a patient, said cardiac monitor including a sensor that senses the intrinsic activity of a patient's heart and generates a corresponding sensed signal; an interval detector that detects the interval associated with a cardiac cycle based on said sensed signal; a waveform factor detector that detects a waveform factor from said sensed signal, said waveform factor being a function of a mean value of said signal during a cardiac cycle and a peak value of said signal during said interval; and a first comparator that compares said waveform factor to a threshold and generates a corresponding first output indicative of the patient's cardiac condition.

The monitor may further include a waveform factor irregularity detector that detects a sudden change in said waveform factor and generates a corresponding second output. A second comparator may be used that compares the second output to a second threshold, said second comparator generating a comparator output indicative of one of ventricular tachycardia and ventricular fibrillation based on said comparator output.

In another aspect of the invention, a method of analyzing the cardiac condition of a patient's heart is provided comprising the steps of sensing a cardiac signal; determining a cardiac interval; determining a waveform factor based on values of said cardiac signal during said cardiac interval and a peak value of said cardiac signal during said interval; comparing said waveform to a first threshold value; and generating respectively a first output indicative of a nonshockable rhythm and a second output indicative of a shockable rhythm. The step of determining a waveform factor may include averaging values of said cardiac signal over said interval and dividing the resulting average by the peak value during said interval to generate an instant waveform factor.

The method may further include averaging said instant waveform factor over several intervals to obtain said waveform factor, and a waveform factor irregularity parameter indicative of a sudden change in said waveform factor. According to the method, a tachyarrhythmia signal is generated if said heart rate exceeds a first threshold and one of a shockable and a nonshockable signal is also generated dependent on a magnitude of said waveform factor, wherein a nonshockable signal is indicative of a supraventricular tachycardia and a shockable signal is indicative of a shockable tachycardia.

In another aspect of the invention, one of a fibrillation and a tachycardia signal is generated dependent on a magnitude of said waveform factor irregularity, said fibrillation signal being indicative of a ventricular fibrillation and said tachycardia signal being indicative of a ventricular tachycardia.

The device and method described can be implemented in either an external or an internal antitachyarrhythmia device.

BRIEF DESCRIPTION OF THE DRAWINGS

These and various other features and advantages of the present invention will be more fully understood with reference to the following detailed description taken in conjunction with the accompanying drawings in which.

DETAILED DESCRIPTION OF THE PREFERRED EMBODIMENT

In overview, the preferred embodiment of the present invention encompasses an arrhythmia detector with a novel detection algorithm which can be used in conjunction with conventional diagnosis algorithms or can be used to provide stand-alone diagnosis of ECG arrhythmias. The method of the invention enables discrimination between ventricular and supraventricular tachyarrhythmias, and discrimination between different ventricular tachyarrhythmias (VT and VF) as well. For example, the novel detection algorithm of the present invention can be used to independently qualify a cardiac rhythm which has been preliminarily diagnosed as a tachyarrhythmia by rate algorithm as being either a ventricular or supraventricular tachyarrhythmia, and then further classify the diagnosed ventricular tachyarrhythmia as VT or VF.

Figure 1:
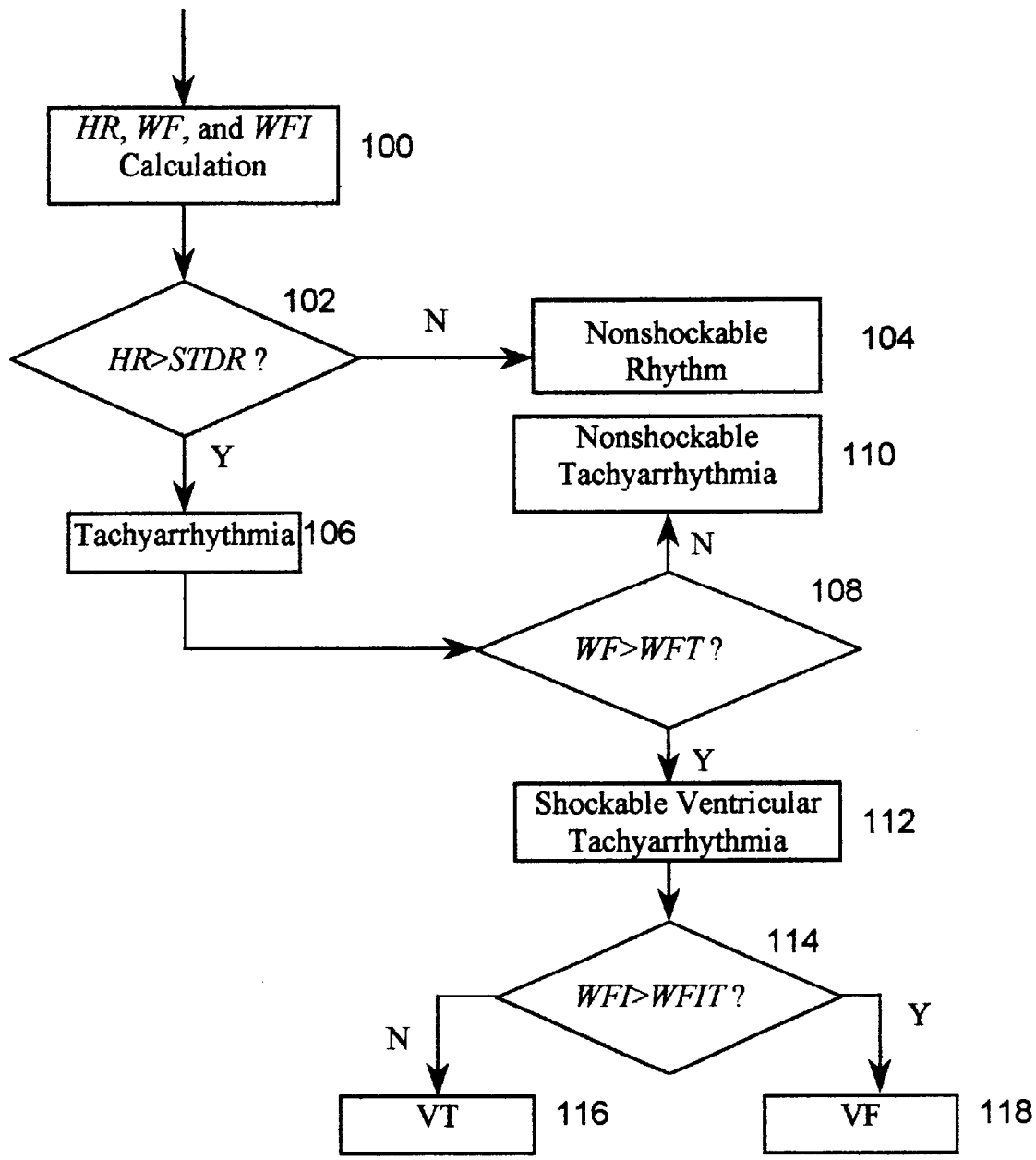
FIG. 1 is a flowchart for the operation of the arrhythmia detector of FIGS. 1A and 1B using an ECG waveform-factor (WF) and a waveform-factor irregularity (WFI) in accordance with the principles of the present invention.
Figure 1A:
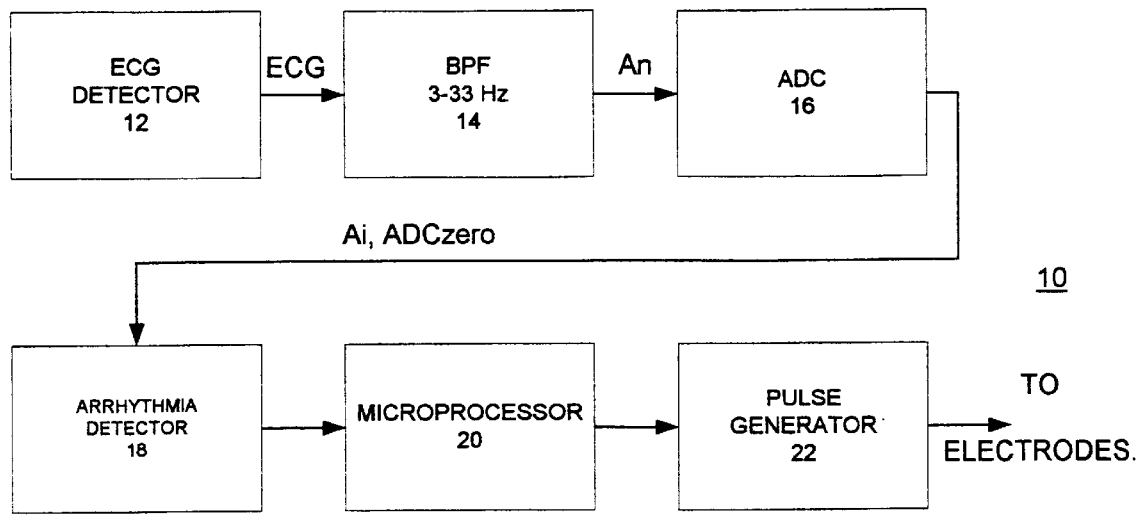
FIG. 1A shows a block diagram of a cardioverter/defibrillator constructed in accordance with this invention.

FIG. 1A shows a block diagram of a cardioverter/defibrillator device 10 constructed in accordance with this invention. Device 10 may be either an implantable or an external device. The device includes an ECG sensor 12 which covers generically any type of sensor that may be used to acquire an ECG signal from a patient, such as the signal shown in FIG. 1C. The ECG signal thus obtained is fed to a band-pass filter 14 which filters the signal from the sensor 12 to pass signals in the rage of about 3–33 Hz. The filtered analog signal $A_n$ is fed to an analog-to-digital converter (ADC) 16. The ADC samples the analog signal $A_n$ at a predetermined rate, such as 128/second or 256/second, and generates two signals $A_i$ and ADCzero. $A_i$ is the amplitude of the current sample, and ADCzero defines the isoelectric baseline of the ECG.

The signals Ai and ADCzero are fed to an arrhythmia detector 18 which determines whether the patient's heart is beating at a sinus rhythm or whether an arrhythmia has been detected that requires therapy. This information is provided to a microprocessor 20 which controls the operation of the device 10. The microprocessor analyzes the signals received from the arrhythmia detector 18 and, if necessary, activates a pulse generator 22. The pulse generator then generates appropriate signals, including for example, cardioversion pulses or defibrillation shocks. These therapy signals are then provided to one or more therapy delivery electrodes 24.

The arrhythmia detector 18 may be incorporated into the microprocessor 20 where it may be implemented by software, however, it is shown here as a separate element for the sake of clarity.

Figure 1B:
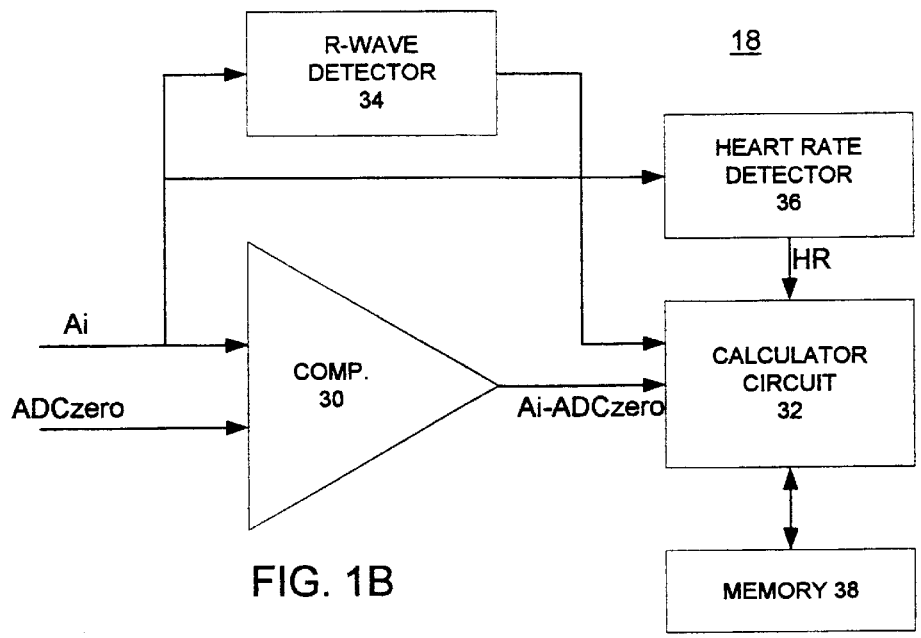
FIG. 1B shows a block diagram of the arrhythmia detector used in the cardioverter/defibrillator of FIG. 1A.
Figure 1C:
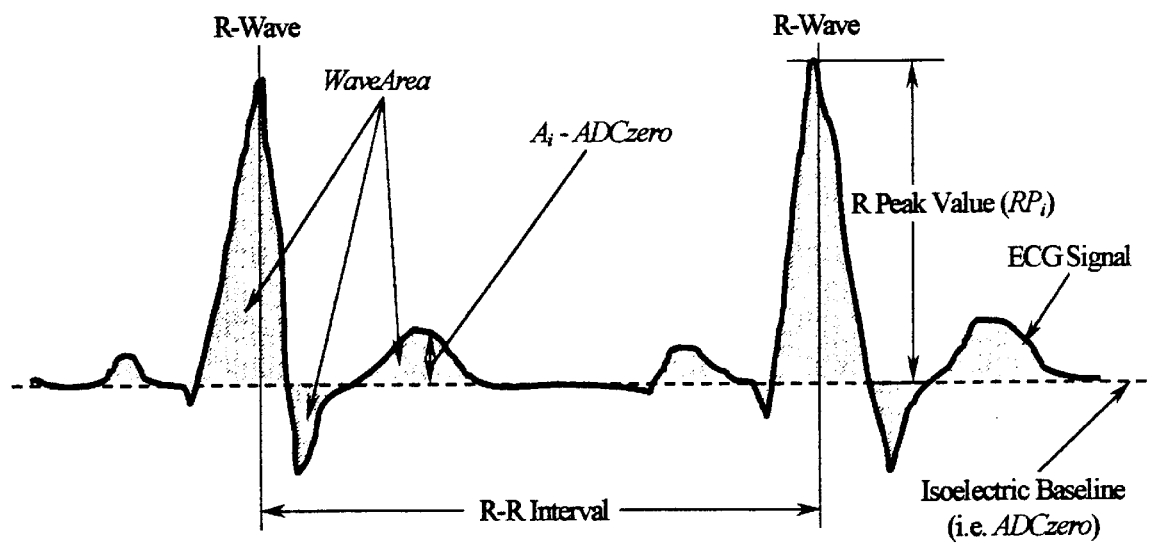
FIG. 1C shows a typical ECG and various parameters thereof used by the present invention.

Referring to FIG. 1B, the arrhythmia detector 18 includes a comparator 30, a calculator circuit 32, an R-wave detector 34, heart rate detector 36 and a memory 38. The operation of the device 10 and its arrhythmia detector 18 is now described.

Now referring to FIG. 1 at step 100, the current heart rate (HR), a waveform-factor (WE), and a waveform-factor irregularity (WFI) are calculated from ECG signal by the detector 18, as discussed in more detail below. At step 102, the current HR is compared to a preset tachyarrhythmia detection rate (STDR) threshold. If HR rises over STDR, then a tachyarrhythmia condition is determined in step 106. Otherwise, normal or supraventricular rhythm is determined in step 104, i.e. a rhythm is determined which does not require any electrical therapy. A typical value for preset tachyarrhythmia detection rate STDR may be about 120 beats per minute.

If tachyarrhythmia is determined in steps 102 and 106 then at step 108 the waveform factor parameter WF is compared to a preset waveform-factor threshold (WFI). A typical value for the parameter WFT may be in the range of 25–35 with 30 (in percentile) being preferable.

If WF is larger than the WFT, then at step 112 it is determined that the tachyarrhythmia is a shockable ventricular tachyarrhythmia. Otherwise, a nonshockable tachyarrhythmia condition is determined in step 110, including supraventricular tachycardia, atrial fibrillation, etc., and no therapy is applied.

Following the determination at step 112, at step 114 the WFI is compared to a pre-set threshold (WFIT). A typical value for WFIT may be about 10. If the current WFI exceeds WFIT, then the ventricular tachyarrhythmia is determined to be ventricular fibrillation (VF) at step 118. Otherwise, at step 116 a ventricular tachycardia is determined. As part of steps 116 and 118 appropriate therapy is generated by the pulse generator 22 and fed to the appropriate electrodes (not shown).

Figure 2:
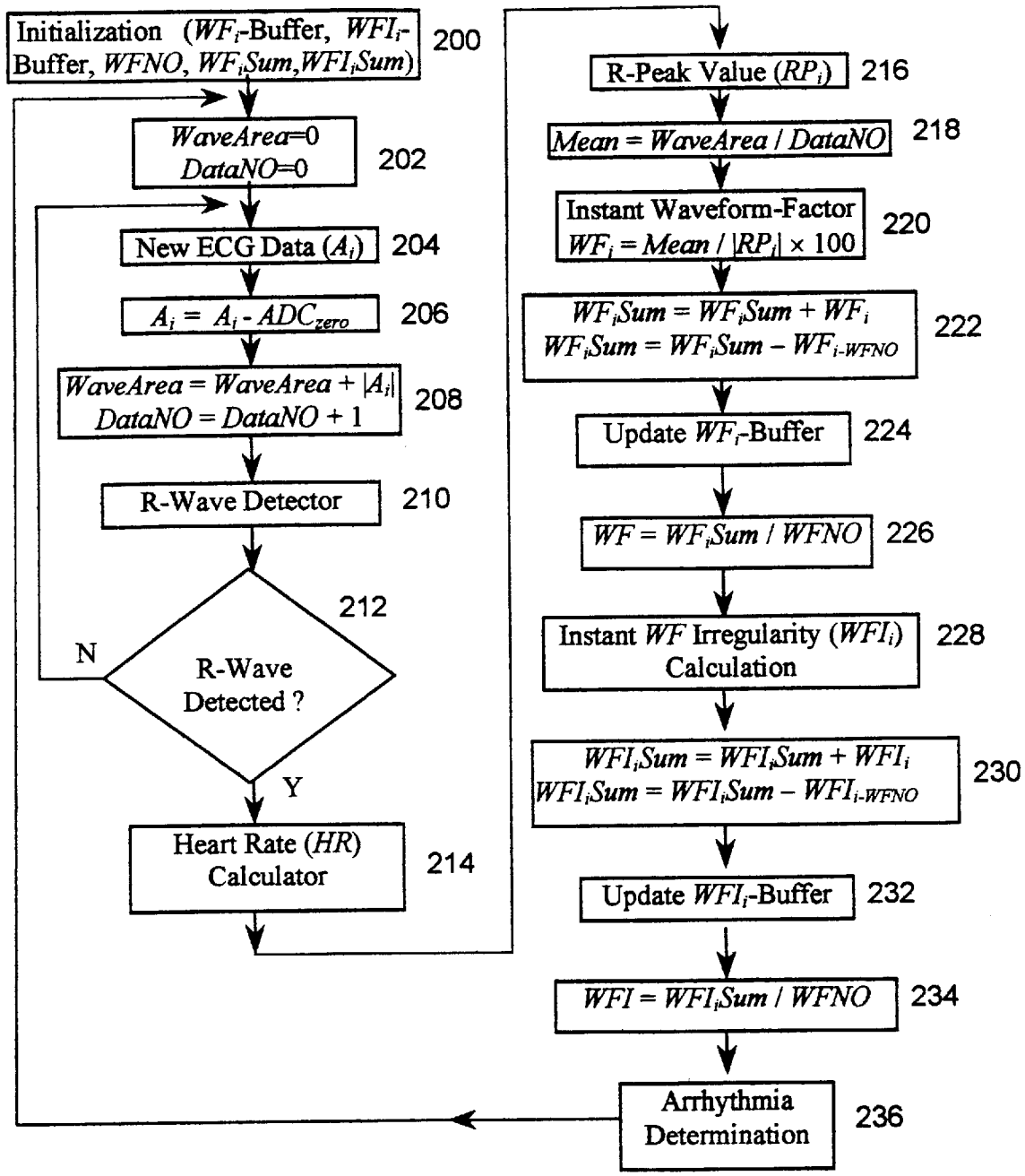
FIG. 2 is a flow chart illustrating the method to estimate the waveform-factor, waveform-factor irregularity from ECG signal.

The calculations required to determine the variables HR, WF, and WFI are now described in conjunction with in FIG. 2. In step 200, some buffers and variables stored in memory 38 are initialized to zero. These include a buffer for storing the values of a predetermined number of consecutive instant waveform-factors ($WF_i$) used to calculate the parameter WF by averaging $WF_i$'s; and a buffer for storing consecutive instant waveform-factor irregularities ($WFI_i$) to calculate the WFI by averaging $WFI_i$'s. These buffers must be sufficient large to hold WFNO data, where WNFO indicates the number of the estimated $WF_i$'s and $WFI_i$'s for a predetermined number of R-waves. In a preferred embodiment, the the estimated $WF_i$'s and $WFI_i$'s during eight consecutive R waves are stored, it being understood that the parameter WNFO may be selected using other criteria as well.

At step 202, the variables WaveArea and DataNO are set to zero every time an R-wave is detected by detector 34. At step 204, a new ECG data $A_i$ is acquired and read into the memory 38 for processing. Before being digitized by the ADC 16 (e.g. 12-bit), the analog ECG signal is filtered with the band-pass filter 14 preferably in the range of 3 to 33 Hz (−3 dB). The low-pass section of the filter serves as an anti-aliasing filter and smooths the transitions in the ECG so that the peaks may easily be identified. The highpass section of the filter 14 serves to remove any baseline drift from the signal, so that a separate DC removal stage is not required.

The filtered analog signal $A_n$ is converted by ADC 16 into a corresponding sample $A_i$ and the parameter ADCzero (i.e. isoelectric baseline) is also generated. For example, A 12-bit ADC can fully have 4095 ADC units to represent a bipolar ECG signal sample $A_i$. Under this situation, an $A_i$ with 2048 ADC units is 0 mV (i;e., ADCzero or isoelectric baseline) in physical value, an $A_i$ with 4095 ADC units is +5 mV, and an $A_i$ with 0 ADC units is −5 mV.

In step 206 the value ADCzero is subtracted from the $A_i$ by comparator 30. Then the absolute value of the difference (i.e. $|A_i-ADCzero|$) is added to the parameter WaveArea and the number of data points DataNO is incremented by one at step 208.

In step 210 the R-wave detector 34 is used to detect the R-wave. The R-wave detector can be implemented using different schemes well known in the art. For example, if the absolute value of $A_i$ exceeds a threshold that is a function of the peak amplitude of the last R-wave and a fixed threshold, a synchronous R impulse is emitted indicating by its presence that the R-wave is recognized.

At step 212 if an R-wave is not detected, the microprocessor 20 continues to acquire the next new data $A_i$ (returning to step 204) and process until an R-wave is detected by detector 34.

If an R-wave is detected then the calculator circuit 32 starts calculating the heart rate HR, the waveform factor WF, and waveform factor irregularity WFI parameters. More specifically, in step 214, the calculator circuit 32 calculates the heart rate HR from a running average of the duration of a prescribed number (e.g. 8) of the latest R-R intervals. Alternatively, a number of R-R intervals are reviewed, any individual interval in exceeding or following below a certain level by a predetermined percentage is discarded and only the remaining intervals are averaged.

At step 216, current R-wave peak value $RP_i$ is selected from the memory 38. Then in step 218, for current R-R interval, the mean amplitude value Mean is estimated by dividing the WaveArea by DataNO.

Next, the current instant waveform-factor ($WF_i$) is calculated at step 220 using the formula $$WF_i = Mean/|RP_i|*100$$

$WF_i$ is obtained just from the ECG data acquired in current R-R interval, therefore, it is called the instant WF for characterizing the ECG waveform. To obtain a relatively stable WF, the following steps 222–226 average the latest WFNO (e.g. 8) data of $WF_i$'s in the buffer of memory 36. At step 222, current $WF_i$ is added to $WF_i$Sum (storing the sum of the latest WFNO data of the $WF_i$'s) and the oldest WF (i.e. $WF_{i-WFNO}$) is subtracted.

The $WF_i$-Buffer is allocated as follows: $WF_{i-WFNO}$, $WF_{i-(WFNO-1)}$, $WF_{i-(WFNO-2)}$, ..., $WF_{i-2}$, $WF_{i-1}$. At step 224, the $WF_i$-Buffer is updated by shifting left one data, and the current $WF_i$ is stored into the position of $WF_{i-1}$ and the oldest one $WF_{i-WFNO}$ shifted out and discarded. Thus, $WF_i$-Buffer always keeps the latest WFNO (e.g. 8) data of the $WF_i$'s. At step 226, the value of WF is calculated by averaging the latest WFNO data of the $WF_i$'s.

The instant waveform-factor irregularity ($WFI_i$) is calculated at step 228 using the formula:

$$WFI_i = |WF_{i-1} WF_{i-2}|/WF_{i-1}*100$$

where, $WF_{i-1}$ in the $WF_i$-Buffer is the current $WF_i$ and $WF_{1-2}$ the previous one, since $WF_i$-Buffer has been updated in step 224. This parameter $WFI_i$ provides an indication of a sudden change of parameter $WF_i$.

Next, the waveform irregularity parameter WFI is calculated. At step 230, the current $WFI_i$ is added to $WFI_i$Sum (storing the sum of the latest WFNO data of the $WFI_i$'s) and the oldest $WFI_i$ (i.e. the one No. WFNO in the buffer, $WFI_{i-WFNO}$) is subtracted. The $WFI_i$-Buffer is allocated as follows: $WFI_{i-WFNO}$, $WFI_{i(WFNO-1)}$, $WFI_{i-(WFNO-2)}$, ..., $WFI_{i-2}$, $WFI_{i-1}$. At step 232, the $WFI_i$-Buffer is updated by shifting left one data, and the current $WFI_i$ is stored into the position of $WFI_{i-1}$ and the oldest one $WFI_{i-WFNO}$ shifted out and discarded. Thus, $WFI_i$-Buffer always keeps the latest WFNO data of the $WFI_i$'s. At step 234, the value of WFI is calculated by averaging the latest WFNO data of the $WFI_i$'s.

At step 236, the estimated parameters HR, WF, and WFI are used for arrhythmia determination as discussed above at steps 102 to 118 in FIG. 1. After finishing arrhythmia discrimination on current cardiac episode, the algorithm starts next operation cycle by returning to step 202. The HR, WF, and WFI are re-computed (updated) in real time every R-R interval (i.e., on an interval-by-interval basis).

As demonstrated above, the novel arrhythmia detector proposed in present invention has following advantages:

1) It is computationally simple, easy to implement by software or hardware (either in analog electronics, or with low computational requirements on a digital microprocessor). All the processing is done using integer arithmetic without requiring excessive computing power. The calculation of parameters WF and WFI does not require too much memory either. Only two buffers are required, each holding WFNO (e.g. 8) data of the parameters $WF_i$ and $WFI_i$.

2) Multiple functions are performed, including discriminating shockable VT and VF from nonshockable SVT (the main cause of false therapy), differentiating VT and VF, thereby providing specific therapies for different arrhythmias.

3) It can track closely the change of the ECG signal rapidly in real time and identify any possible VF or VT for timely suitable therapy (i.e., high-energy defibrillation, low-energy cardioversion, etc.). Unnecessary shock therapy for SVT is also avoided since the arrhythmia detection is performed every R-R interval.

4) ECG dropout is tolerated. As illustrated in FIG. 2, if one R-wave is missed, more ECG data is collected for calculating $WF_i$. Since $WF_i$ is an average based on a predetermined number of ECG samples (DataNO), it will still be an accurate factor characterizing the ECG waveform morphology, even if its collected over a longer segment (two R-R intervals). Measuring cycle length (i.e., heart rate HR) is dependent on an accurate sensing of R-wave.

Although the present invention has been described in detail hereinabove, it should be clearly understood that many alternatives to the embodiments and/or modifications of the basic inventive concepts herein taught which may appear to those skilled practitioner will still fall within the spirit and scope of the present invention, as defined in the claims. For examples, at step 108 (or 114), by checking whether a predetermined number or proportion of a series of preceding WF's (or WFI's) are greater than the preset threshold WFT (or WFIT) to determine the arrhythmia is shockable tachyarrhythmia(or VF)(e.g. at least 4 of the preceding 6 estimated WF's (or WFI's) over the preset threshold); or by using WF (or WFI) related concepts, such as "onset" to detect arrhythmias; or at step 226 (or 234), by discarding a percentage of $WF_i$'s (or $WFI_i$'s) prior to averaging them to get WF (or WFI) (e.g., discarding the largest and smallest ones among WFNO data; or first discarding the one with the largest difference to the average of these WFNO data, and then among the remaining WFNO-1 data discarding the one with the largest difference to the average of the remaining WFNO-1 data, finally averaging the remaining WFNO-2 data); or just triggering the calculation of WFI at step 112 each time the detected WF exceeds a pre-set threshold WFT.

The present invention will be further understood according to the following description of specific examples.

EXAMPLES

The ECG signals were digitized in the rate of 128 samples per second with a 12-bit A/D resolution, and as described above in FIGS. 1A, 1B, 1 and 2.

Figure 3A:
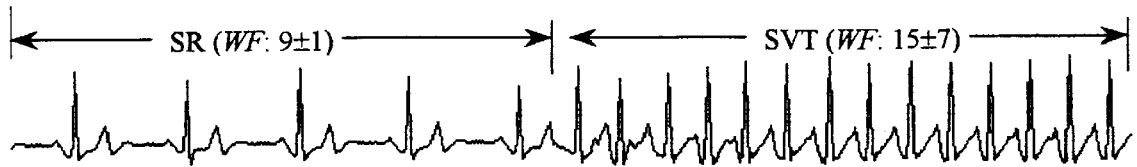
FIGS. 3A–3E illustrate exemplary nonshockable ECG waveforms of sinus rhythm (SR), supraventricular tachycardia (SVT), sinus tachycardia (ST), and atrial fibrillation (AF), along with the corresponding waveform-factor (WF) statistical values (mean ±Standard Deviation, SD).
Figure 3B:
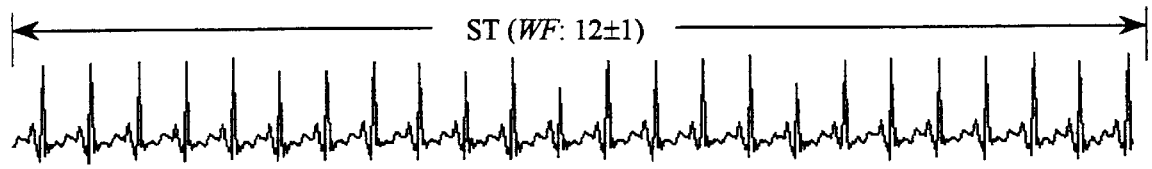
Figure 3C:
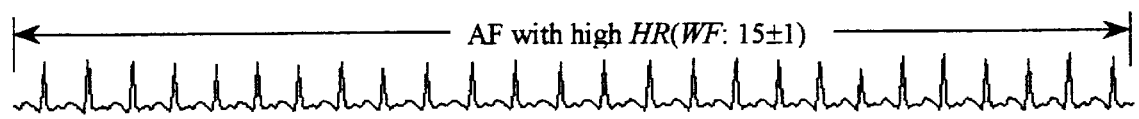
Figure 3D:
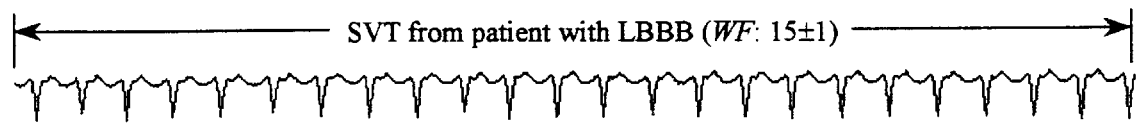
Figure 3E:
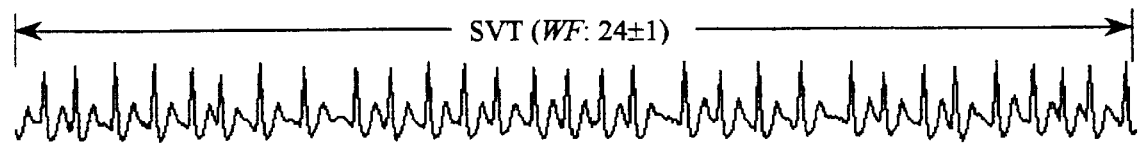

First, some nonshockable rhythms and their WF statistical values (mean ±SD) are illustrated in FIGS. 3A–3E. An example of sinus rhythm (SR) suddenly changing into supraventricular tachycardia (SVT) is shown in FIG. 3A. An example of sinus tachycardia (ST) is shown in FIG. 3B, an example of atrial fibrillation (AF) with high heart rate (HR) in FIG. 3C, an example of SVT from patient with left bundle branch block (LBBB) is shown in FIG. 3D, and another example of SVT with aberrant conduction is shown in FIG. 3E. The WF values for each of these rhythms are all below one threshold (such as 30 percent). For these nonshockable rhythms, the waveform-factor irregularity (WFI) does not need to be calculated. The value of parameter WF for these waveforms is listed below:

| WAVEFORM TYPE | WF | FIG. |
|---|---|---|
| SINUS RHYTHM | 9 ± 1 | 3A |
| SVT | 15 ± 7 | 3A |
| ST | 12 ± 1 | 3B |

-continued

| WAVEFORM TYPE | WF | FIG. |
|---|---|---|
| AF WITH HIGH HR | 15 ± 1 | 3C |
| SVT WITH LBBB | 15 ± 1 | 3D |
| SVT | 24 ± 1 | 3E |

Figure 4A:
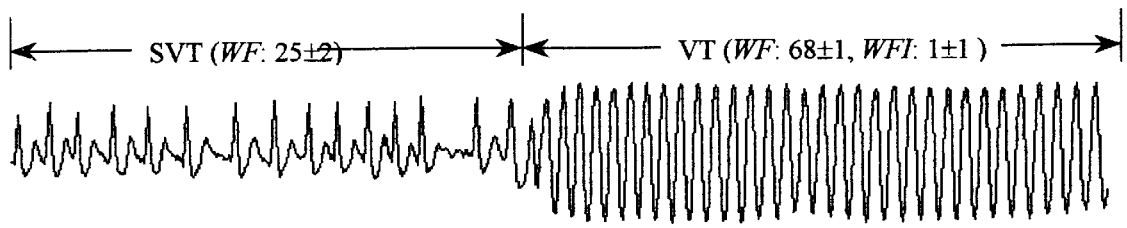
FIGS. 4A–4E illustrate exemplary shockable ECG waveforms of ventricular tachycardia (VT), ventricular fibrillation (VF), and fine VF, along with the corresponding WF and WF irregularity (WFI) statistical values (mean ±SD).
Figure 4B:
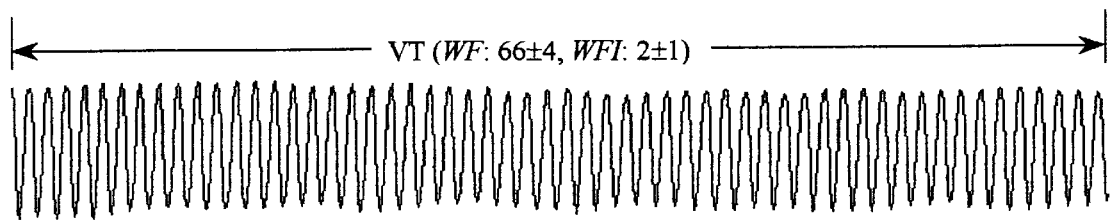
Figure 4C:
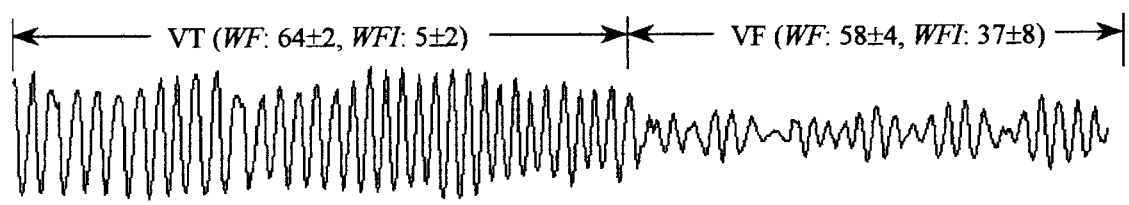
Figure 4D:
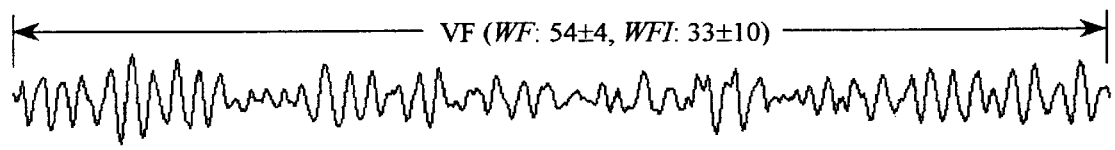
Figure 4E:
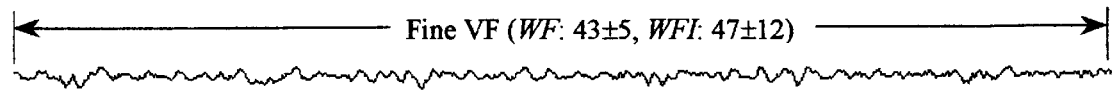

Several shockable tachyarrhythmias and their WF and WFI statistical values are illustrated in FIGS. 4A–4E. More specifically, an example of SVT suddenly changing into VT is shown in FIG. 4A, an example of VT is shown in FIG. 4B, an example of VT changing into VF is shown in FIG. 4C, an example of VF is shown in FIG. 4D, and an example of fine VF is shown in FIG. 4E.

Values for the parameters WF and WFI for the waveforms of FIGS. 4A–4E are listed below:

| WAVEFORM TYPE | WF | WFI | FIG. |
|---|---|---|---|
| SVT | 25 ± 2 | N.A. | 4A |
| VT | 68 ± 1 | 1 ± 1 | 4A |
| VT | 66 ± 4 | 2 ± 1 | 4B |
| VT | 64 ± 2 | 5 ± 2 | 4C |
| VF | 58 ± 4 | 37 ± 8 | 4C |
| VF | 54 ± 4 | 33 ± 10 | 4D |
| fine VF | 43 ± 5 | 47 ± 12 | 4E |

The WF values for these arrhythmias are all over one threshold (such as 30 percentile). Moreover the WFI values for VF and fine VF are much higher than for VT. By using WFI, VF and VT can be thus differentiated from each other. More particularly in step 114 in FIG. 1 the value of threshold WFIT may be in the range of 5–15 with 10 (in percentile) being preferable.

Figure 5:
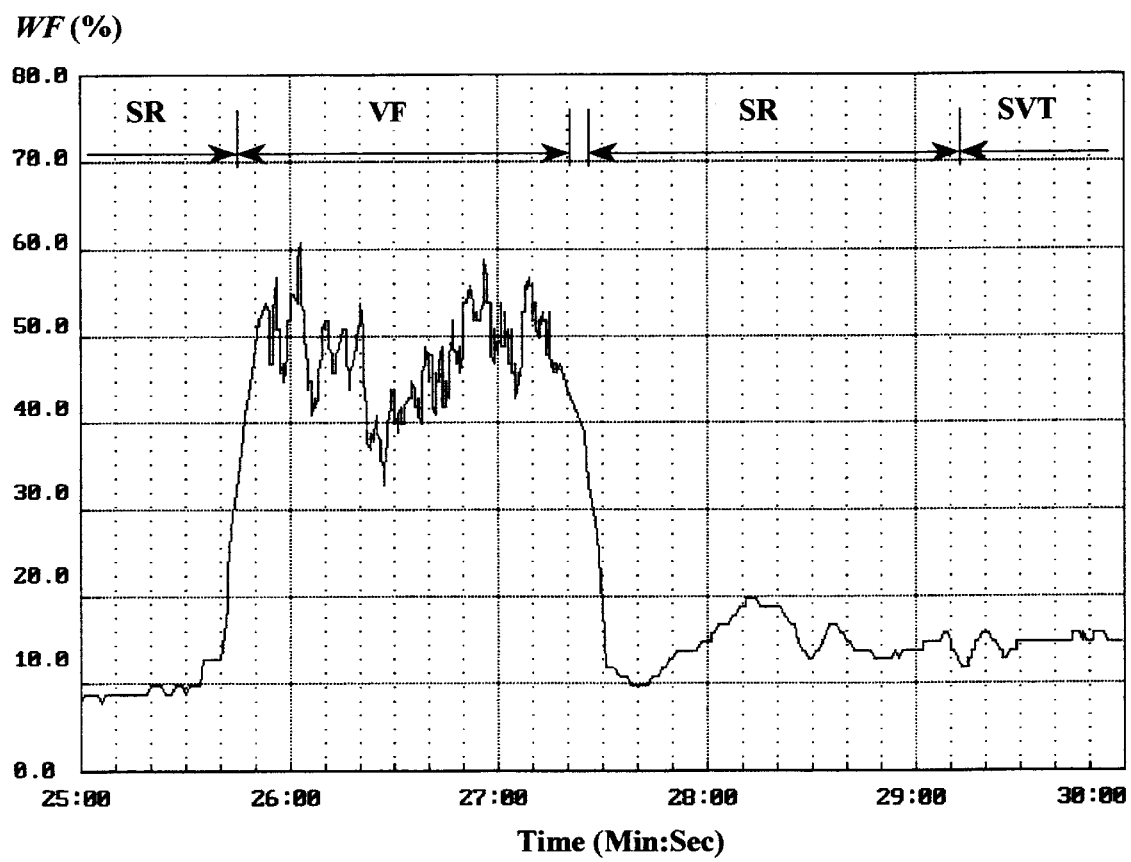
FIG. 5 is an exemplary sample showing the estimated waveform-factor (WF) (every R-wave one WF) changing with rhythms in real time (from SR to VF to SR to SVT).

By comparing FIG. 3A and FIG. 4A, it is found that sudden onset of a high rate is not a reliable means of discriminating SVT from VT, since sometime SR can suddenly change into SVT just as SVT suddenly changes into VT. However, by using WF, SVT can be easily differentiated from VT, since SVT has a lower WF value. For every R-wave detected one WF value is calculated by averaging the latest eight instant waveform-factors ($WF_i$). FIG. 5 demonstrates how WF tracks the changes of rhythms (from SR to VF to SR to SVT) during one 5-min recording. The onset of shockable VF definitely can be identified by a WF threshold (such as 30 percentile) from other nonshockable rhythms.

Although body surface ECG used by AED is utilized here as examples to illustrate the invention, epicardiac or intracardiac electrogram used by ICD or pacemaker are also suited for being analyzed by the present invention. Numerous modifications may be made to this invention without departing from its scope as defined in the appended claims.

We claim:

1. A cardiac monitor for determining the cardiac condition of a patient comprising:
    a sensor that senses the intrinsic activity of a patient's heart and generates a corresponding sensed signal;
    an interval detector that detects an interval associated with a cardiac cycle based on said sensed signal;
    a waveform factor detector that detects a waveform factor from said sensed signal, said waveform factor being a function of a ratio of a mean value of said signal during said cardiac cycle and a peak value of said signal during said interval; and a first comparator that compares said waveform factor to a threshold and generates a corresponding for first output indicative of the patient's cardiac condition.

2. The cardiac monitor of claim 1 further comprising a waveform factor irregularity detector that detects a sudden change in said waveform factor and generates a corresponding second output.

3. The cardiac monitor of claim 2 further comprising a second comparator that compares said second output to a second threshold, said second comparator generating a comparator output indicative of one of ventricular tachycardia and ventricular fibrillation based on said comparator output.

4. The cardiac monitor of claim 2 wherein said waveform factor irregularity detector further includes an averager that averages a waveform factor irregularity over several cardiac cycles to generate an irregularity average indicative of one of a tachycardiac and ventricular fibrillation condition.

5. The cardiac monitor of claim 1 wherein said cardiac monitor is external.

6. The cardiac monitor of claim 1 wherein said cardiac monitor is implantable.

7. The cardiac monitor of claim 1 wherein said cardiac monitor is incorporated into an internal defibrillator.

8. The cardiac monitor of claim 1 wherein said cardiac monitor is incorporated into an external defibrillator.

9. The cardiac monitor of claim 1 wherein said sensor signal is an ECG.

10. The cardiac monitor of claim 1 wherein said waveform factor detector detects a plurality of instant waveform factors, each instant waveform factor being derived from the ratio of between said mean value and said peak value.

11. The cardiac monitor of claim 10 wherein said waveform factor detector detects said instant waveform factors based on said mean value, wherein said mean value is determined from an area under said sensed signal and a current R-wave peak value of said sensed signal.

12. The cardiac monitor of claim 10 wherein said waveform factor detector determines said waveform factor by averaging said plurality of instant waveform factors.

13. The cardiac monitor of claim 2 wherein said waveform factor irregularity detector generates a waveform factor irregularity based on a difference between two consecutive waveform factors.

14. A cardiac therapy device adapted to selectively provide shock therapy to a patient, comprising:

a sensor adapted to detect intrinsic activity in the patient's heart and to generate a corresponding sensed signal;

a pulse generator adapted to generate therapy pulses in response to control signals;

a monitor adapted to classify a cardiac condition and to generate a corresponding heart condition signal; and a controller adapted to receive said heart condition signal and to generate in response said control signals;

wherein said monitor includes:

an interval detector that detects an interval associated with a cardiac cycle based on said sensed signal;

a waveform factor detector that detects a waveform factor from said sensed signal, said waveform factor being a function of a ratio of a mean value of said sensed signal during said cardiac cycle and a peak value of said sensed signal during said interval; and a first comparator that compares said waveform factor to a threshold and generates a corresponding first output indicative of the patient's cardiac condition.

15. The device of claim 14 wherein said monitor further comprises a waveform factor irregularity detector that detects a sudden change in said waveform factor and generates a corresponding second output.

16. The device of claim 15 wherein said monitor further comprises a second comparator that compares said second output to a second threshold, said second comparator generating a comparator output indicative of one of ventricular tachycardia and ventricular fibrillation based on said comparator output.

17. The device of claim 15 wherein said waveform irregularity detector further includes an averager that averages said waveform irregularity over several cardiac cycles to generate an irregularity average indicative of one of a tachycardiac and ventricular fibrillation condition.

18. The device of claim 14 wherein said device is external.

19. The device of claim 14 wherein said device is implantable.

20. The device of claim 14 wherein said sensed signal is an ECG.

* * * * *